US009965594B2

(12) United States Patent
Portney

(10) Patent No.: US 9,965,594 B2
(45) Date of Patent: May 8, 2018

(54) DIGITAL DISPENSER SYSTEM

(76) Inventor: Nathaniel Gerald Portney, Newport Coast, CA (US)

( * ) Notice: Subject to any disclaimer, the term of this patent is extended or adjusted under 35 U.S.C. 154(b) by 598 days.

(21) Appl. No.: 13/204,407

(22) Filed: Aug. 5, 2011

(65) Prior Publication Data
US 2012/0035760 A1 Feb. 9, 2012

Related U.S. Application Data

(60) Provisional application No. 61/371,371, filed on Aug. 6, 2010.

(51) Int. Cl.
*G06F 17/00* (2006.01)
*G06F 19/00* (2018.01)

(52) U.S. Cl.
CPC ..... *G06F 19/3462* (2013.01); *A61M 2205/35* (2013.01); *A61M 2205/3569* (2013.01)

(58) Field of Classification Search
CPC .......... G06F 19/3462; A61M 2205/35; A61M 2205/3569
USPC .................................................. 700/231–244
See application file for complete search history.

(56) References Cited

U.S. PATENT DOCUMENTS

| 5,036,462 | A | * | 7/1991 | Kaufman et al. ............. 600/300 |
| 5,409,132 | A | * | 4/1995 | Kooijmans et al. ............. 221/86 |
| 5,582,323 | A | * | 12/1996 | Kurtenbach .......... A61J 7/0481 221/2 |
| 6,234,343 | B1 | * | 5/2001 | Papp ................................ 221/7 |
| 6,439,422 | B1 | * | 8/2002 | Papp et al. ...................... 221/13 |
| 6,510,962 | B1 | * | 1/2003 | Lim ..................... A61J 7/0481 221/15 |
| 6,601,729 | B1 | * | 8/2003 | Papp ............................. 221/25 |
| 6,651,840 | B1 | * | 11/2003 | Van Dullemen et al. ...... 221/88 |
| 6,702,146 | B2 | * | 3/2004 | Varis ............................... 221/3 |
| 7,284,678 | B2 | * | 10/2007 | Bloom .................... G07F 9/026 221/150 R |
| 7,302,311 | B2 | * | 11/2007 | Varis ............................ 700/232 |
| 7,369,919 | B2 | * | 5/2008 | Vonk et al. ................... 700/236 |
| 7,440,817 | B2 | * | 10/2008 | Fu ................................ 700/237 |
| 7,537,005 | B2 | * | 5/2009 | Dave ........................ 128/200.14 |
| 7,743,923 | B2 | * | 6/2010 | Conley ..................... 206/534.1 |
| 7,801,745 | B2 | * | 9/2010 | Walker et al. ................... 705/2 |
| 7,805,216 | B2 | * | 9/2010 | Shows et al. ................ 700/231 |
| 7,825,808 | B2 | * | 11/2010 | Kim ......................... 340/572.4 |
| 7,896,192 | B2 | * | 3/2011 | Conley et al. .................. 221/15 |
| 7,996,106 | B2 | * | 8/2011 | Ervin .......................... 700/237 |
| 8,061,351 | B2 | * | 11/2011 | Dave ........................ 128/200.14 |
| 8,086,350 | B2 | * | 12/2011 | Timmermans et al. ...... 700/242 |
| 8,095,235 | B2 | * | 1/2012 | Tzeng et al. ................. 700/232 |
| 8,135,497 | B2 | * | 3/2012 | Joslyn .......................... 700/237 |
| 8,397,946 | B2 | * | 3/2013 | Portney ............. B65D 83/0454 221/113 |
| 2004/0158350 | A1 | * | 8/2004 | Ostergaard et al. .......... 700/231 |
| 2005/0150488 | A1 | * | 7/2005 | Dave ........................ 128/200.14 |
| 2005/0177275 | A1 | * | 8/2005 | Harvey et al. ................ 700/244 |
| 2008/0312604 | A1 | * | 12/2008 | Boesen ........................ 604/207 |

(Continued)

*Primary Examiner* — Michael Collins
(74) *Attorney, Agent, or Firm* — Hackler Daghighian Martino & Novak

(57) ABSTRACT

A digital dispenser system including a cartridge for storing a supply of medicament, a mechanical dispenser for metering medicament out of the cartridge, and a communication system established between the cartridge and the dispenser for relaying information about the medicament stored and dispensed.

17 Claims, 3 Drawing Sheets

(56) References Cited

U.S. PATENT DOCUMENTS

2009/0315702 A1* 12/2009 Cohen Alloro et al. ... 340/539.1
2010/0168910 A1*  7/2010 Haas .............................. 700/232
2010/0312383 A1* 12/2010 Naik et al. .................... 700/242
2012/0035760 A1*  2/2012 Portney ......................... 700/231
2014/0026887 A1*  1/2014 Portney .................... 128/203.21

* cited by examiner

DIGITAL DISPENSER SYSTEM

The present application claims priority from U.S. Ser. No. 61/371,371 filed Aug. 6, 2010. This patent application is to be incorporated herewith in its entirety by the specific reference thereto.

BACKGROUND OF THE INVENTION

It has been demonstrated statistically, that medication delivered in pill dispensers are two times less likely to be in error than delivered in free form[1], thereby making pill dispensers a cost and health saving aspect in health management. (The Influence of Formulation and Medicine Delivery System on Medication Administration Errors in Care Homes for Older People. D P Alldred, C Standage, O Fletcher, I Savage, J Carpenter, N Barber, D K Raynor. BMJ Qual Saf 2011; bmjqs.2010.046318 Published Online First; 7 Feb. 2011). Also, there is a substantial array of health management software, intended to facilitate improved medication intake (compliance, adherence), which allows a caregiver or high needs patient to better manage their assortment of medications (e.g. medical scheduling, medication management, e-prescribing, etc).

There are a variety of devices made to improve compliance and adherence of medication. Currently, it is becoming more difficult for patients to coordinate an increasingly complex regimen of pills at the right times. Current systems are pill organizers, and carousel dispensers, and cartridge based dispensers, U.S. patent application Ser. No. 12/840,010 by N. Portney, filed Jul. 20, 2010, intended to help organize the release of pills.

Digital dispensers for syringe usage, U.S. Pat. No. 4,959,056, an automatic pill dispenser, U.S. Pat. No. 5,372,276, used to set pre-programmed supply for memory impaired patients, and an electronic pill reminder device, U.S. Pat. No. 6,545,592 used to timer to aid in timely medication usage are examples.

The current dispensing systems, while offering some degree of reminder, or digital assisted selection, are incapable of tracking the actual medication usage of each discrete tablet. For example, a pill reminder may be able to alert the patient, but has no way of reminding again if turned off. This iterative feedback is an important need to enable better compliance and adherence of medication usage, and is currently unavailable.

Thus, these systems have no way of determining how the patient is in fact taking the medication at the unit level or time basis Other pill devices which have built in reminders are sometimes capable of sending a message to a network to remind the patient to take their medication, but are primitive, because they lack patient feedback in the true time history of the medication dispensed. Furthermore, the prescribing physician in a healthcare setting has no way of digitally monitoring the true dispensing histories of their patients from the medical cabinets. Therefore, an iterative feedback loop is truly required in this industry, to successfully connect all of these components, through an intelligible system before compliance/adherence issues can be better controlled.

Key issues that inhibit development of such an optimal system include (a) control and recording of medication dispensing histories and accountability of each tablet designated to a patient, (b) providing the ability to feedback to the patient to take medication, (c) packaging the system in a practical portable system that patient for easy dispensing. The digital dispenser system in accordance with the present invention, has the capability to achieve all functions, and reduce the non-compliance cost in healthcare industry. The objective of the disclosure is the System, called D-Dispenser that improves the patient's compliance and adherence of any oral dosage formulation (tablet, filled capsule, softgel). This will also physicians to receive feedback of all of their patient medication dispensing histories, and allow them to monitor, analyze, and intervene for better compliance and adherence strategies for improved patient outcomes.

SUMMARY OF THE INVENTION

The objective of this invention is to greatly reduce the costs of non-compliance and adherence in medication usage, and avoid medication error by introducing a digital dispensing system using available RF technology. In our RF system, we position an RFID tag and RFID receiver module to enable reading and transmittance of patient history to an external network. The time stamped eject history at each tablet will provide insight and enable feedback to help guiding the patient for better compliance and adherence of their medication treatment program.

The D-Dispenser may include a Cartridge carrying medication with RF tag or any type of electro-magnetic waves actuator (passive or active) and D-Dispenser itself to encompass the cartridge with RF-reader or sensor and programmable ability (software) to report/alert the user on the dispensing status and optional Station to program a Dispenser and/or collect status of a Dispenser for recording or specialized computer program for use a computer to program the Dispenser. Combination of RF tagged Cartridge, and the RFID reader module embedded Dispenser defines the System. The System allows the relay of information about the medication, the refill need information, benefits and contraindications about the medication, new updates on the medicines. Information may be transmitted over any network. The RFID reader module can capture time stamped data of multiple cartridges loaded over usage histories by the patient, and transmit possible conflicts prescribed by multiple physicians, signaling an alarm feature or triggering a patient call notice. Presence of programming capability also allows inclusion of biometric security access the D-Dispenser, such as a finger-print for instance.

Delivery may be independent upon the order of the filling—program selects the appropriate Cartridge compartment order. The Dispenser includes a shutter to prevent accidental release.

Including of a power source in D-Dispenser may add some extra features such as the LED to light the dispensing elements in low light conditions or cooling element which can be of active cooling by electron means, for instance as Peltier cooling.

U.S. patent application Ser. No. 12/840,010 illustrates a mechanical dispenser which may be used as the mechanical part of the present invention, however other dispenser systems may be utilized. This application is to be incorporated herein in its entirety by this specific reference hereto. The key of the invention is the addition for the RFID tags/receiver to the dispensing cartridge based system for the purpose of recording dispensing and providing feedback information flow to the user or external network.

DETAILED DESCRIPTION

Figure 1:
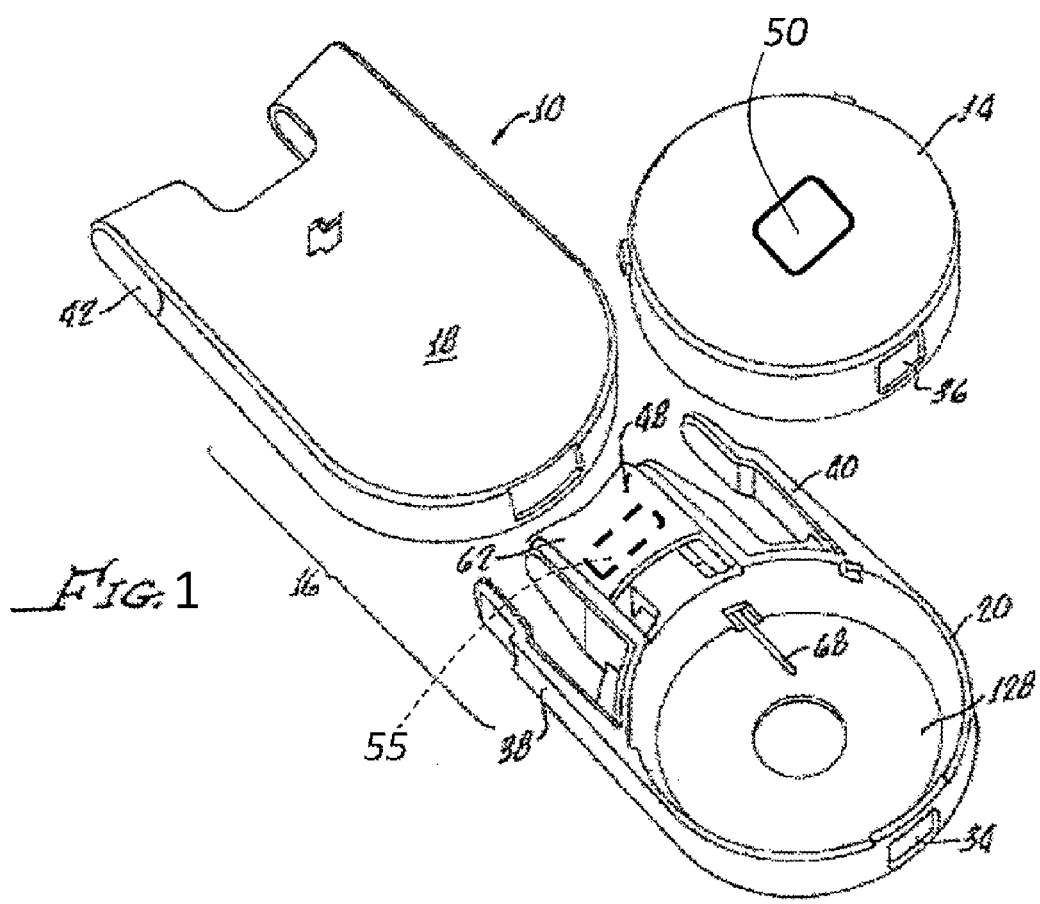
FIG. 1 shows an exploded view of the D-Dispenser illustrating the housing as having a frame and a carrier along with the removable cartridge and a mechanism for rotating the receptacle within the cartridge. A tag (or responder) is affixed to the surface of the cartridge for its identification, and receiver is housed inside the housing itself at the placed where the user interacts with, for instance in the button structure as shown on the FIG. 1. Alternatively, a responder may be placed at the opposite end of the dispenser housing if there is no need for cartridge identification. The key requirement for the responder and receiver positions is that their physical relationship changes in coordination with the medication dispensing to allow the dispensing registration.

The present invention may be better understood with reference to the following detailed description when taken in conjunction with the accompanying drawings, in which:

FIG. 1 shows a cartridge based dispensing system 10 in accordance with the present invention generally illustrating a cartridge 14 and a housing 16 including a frame 18 and a carrier 20 for receiving the cartridge 14. However, some background is provided as previously taught in U.S. Pat. No. 8,397,946, where the carrier 20 further comprises extending spring-like fingers 38, 40 for releasably engaging ends 42, 44 of the frame 18. The release of the carrier 20 from the frame 18 is enabled by squeezing of the fingers 38, 40. A mechanism 48 is provided for rotation of a receptacle within the cartridge 14 in order to align separate compartments 56, 58 with the housing opening 34. This rotation is caused through a linear actuator, such as, for example only, a depressible button 62 of the button 62 being biased by a spring. The mechanism 48 is configured by way of a push rod 68, interconnected with the button 62, and a receptacle 52 configuration including a sprocket 70 disposed for engagement by the push rod 68 with the sprocket having teeth correlated to a number of compartments 56, 58 in an inserted receptacle 52. It should be appreciated that the push rod 68 displacement can be increased to allow the ejection of multiple items 28 under a single button 62 depression. It should be appreciated that while the mechanism 148 is illustrated as being implemented through use of a manually depressible button 62, other configurations may be utilized to operate the push rod 48 and sprocket 70 including electric or electronic devices, not shown. It is important, however, that the mechanism is configured for causing different discrete angular rotations of the receptacle 52 corresponding to compartment 56 of size. With reference now to FIGS. 7-9 of the '946patent, there is shown the cartridge 14 with the receptacle 52 being mounted for rotation within the cartridge 14 via a hub 76. A perimeter sidewall 78 having an opening 80 alignable with the carrier opening 34 enables sealing of the receptacle 52 within the cartridge 40 by way of a cover 84. Reverse rotation of the receptacle 52 within the cartridge 14 is prevented through the use of a dog 88 disposed at a half top 90 of the hub 76 and engagable with a ratchet 92 disposed at a top 94 of the receptacle 52. The present invention further encompasses multiple cartridges 98, 101, 102, see FIGS. 10-15, with corresponding receptacles 106, 108, 110 each having different sized compartments 114, 116, 118 which may be also shaped to accommodate different sized pills or capsules 122, 124, 126 separated. Each of the receptacles 52, 106, 108, are sized for an insertion into a carrier cavity 128, see FIG. 3, with a sprocket 70, 134, 136, 138 engaging a push rod 68. Importantly, the number of teeth 72, 142, 144, 146 are correlated with compartment 56, 114, 166, 118, there being n compartments 56, 114, 116, 118 for n+1 teeth 172, 142, 144, 146.

Now referring back to the present invention, this particular embodiment incorporates the button 48 in a carrier 20 which is extended through the housing 16 upon assembly for push action by the use for medication dispensing form the cartridge 14 through the opening 36 and the opening 34 of the carrier 20.

A tag (or transponder) 50 is affixed to the surface of the cartridge 14. This tag may be also be addressed in each of the partitions of the cartridge chamber for each section. The RFID tag 50 is placed on the cartridge 14 to allow the cartridge identification by the D-Dispenser.

The RFID reader module (receiver) 55 is housed inside the button structure 48. The receiver can be designed to operate with a variety of tags, depending on radio frequency power (eg low frequency at 125 kHz). It is activated when the distance between the transponder 50 and receiver 55 is reduced below the activation limit. This occurs in the given embodiment with the pressing the button by the dispenser user for a pill dispensing.

There is a common need for cartridge identification in order to identify a number compartment and even their content. In this case the transponder 50 is placed at the cartridge.

If there is no need for cartridge identification, the transponder 50 or similar may be placed at the carrier at the opposite side from the button 48, i.e. close to opening 34 to be read when the button is pressing in and the distance between transponder and receiver is reduced below the limit of activation.

The RFID tag (transponder) 50 may be passive RFID, active RFID, or battery assisted passive RFID, smart RFID tag, field programmable RFID tag, chip-less tag. The preferred version of this tag is a passive RFID tag, which enables most affordable usage without requiring an external power supply, suitable for a disposable cartridge. In some applications, using a field programmable RFID tag would allow a cartridge to be reprogrammed for re-use with another drug filling. For example, the patient may return depleted cartridges to a collection facility, which can recycle the cartridge and reprogram the RFID tag for another patient, or use as a same patient refill to reduce waste. Chip-less tags may also be considered due to lowest cost, if only their presence needs to be detected within read range (not product identity).

The configuration is designed such that the resting distance between receiver 55 and tag 50 is greater than the designed interrogation zone (read distance). When the receiver 55 is brought in proximity to the tag 50, sufficient to fall within the interrogation zone, the receiver reads and stores and transmits a history event, or any combination of actions. It is preferable for the receiver module to store and to transmit when requested to conserve the battery. The history event records the act of a tablet ejecting, as the button pressing action approaches the receiver within read range of the tag. For example, in the hand-held D-Dispenser, it is possible to utilize a near-field tag, with high selectivity, to require read distances as low as 1 cm. This distance can be controlled by radio frequency power output of the receiver. A high selectivity is required to ensure there are no partial reads by the receiving antenna. When the receiver 55 is in the relaxed state (eg 3 cm), there is no read/write capture of the tag. As the button 48 is pressed by user, the receiver is able to read from the tag 50, and a time stamped counter is recorded at the receiver location.

The cartridge system receives a RF tag 50, which identifies the content specified (eg drug content), stored in the tag's microchip. This is ideally a passive RF tag, to keep costs low on a disposable cartridge system. Positioning of the tag is at the center of the compartment receptacle (eg 'carousel' part), to keep the separation distance between tag and receiver independent of the rotation of carousel in cartridge system. The RF tag can be lodged in the center cavity and can be outside of the line of site from the receiver. Passive tags used are preferred for cost reduction in overall system design, and close range limitations for passive tagging is satisfactory. Memory of 10s of kbits of data per tag is sufficient to store the complete drug content, as well as patient specific scheduling.

The button 48 of FIG. 1 contains an embedded RFID receiver 55, which is capable of reading the tag 50. The RF-ID arrangement can be designed to reduce the interrogation zone (read distance), by for example, reducing the magnetic field coupling between the receiver and the tag (as low as 1 cm possible).

The receiver is coupled to a microcontroller and flash storage, as part of an embedded RFID reader module 55, all housed within the button cavity structure. There are miniature commercially available RFID reader modules designed to operate with close range passive RFID tags (Parallax RFID Reader Module #28140). The RFID reader embedded module can store (flash memory) and transmit data to a wireless network by another host computer (eg mobile phone, mobile device, data network). Even though recording states are intermittent as button is pressed to fall within read zone, the dwell time requirement is satisfied as the read time required is in milliseconds and tag read rate is high. Additionally, the button housing itself can be designed to be detachable from the device, and have sufficient connectivity (eg RS-232 port standard) within the embedded system to enable direct plug-in to an external device (eg computer port) to read the memory.

As the button 48 approaches the cartridge during each button eject, the reader sends out an RF wave to the RFID tag 50, which is stored on the embedded RFID module 55. Over the course of consumer usage (through button ejections), the RFID module receives series of time stamps of usage for the given tag. Initially, the RFID reader module will record the ID, which defines the cartridge capacity (eg number of compartments), drug/product content, and (when pre-programmed) patient identification, and other pertinent information.

Alternative configuration includes having multiple RFID tags 50 in the compartment chamber of each partition, and the RFID reader module 55 can confirm identity of each compartment for multiple assortment of drugs loaded. For example, medication A will be read when coming into read range of the RFID reader module, then medication B will come in range, etc. Such application would be useful in transmitting warnings about possible drug interactions if the combination of drugs in question were taken too rapidly in succession, posing a health risk.

The positioning of the RFID tag can be on a fixed position of the dispenser body, if the cartridge identity is irrelevant. It must be outside of interrogation zone in relaxed state.

It should be appreciated that the present invention is not limited to RFID technology to provide communication between the cartridge and the dispenser itself. For example, when cartridge identity is irrelevant and cheaper methods are exploited, one can use a switch chip attached to the button housing. When cartridge is inserted, a circuit loop is closed each time the button is pressed and makes contact at pressed point, enabling a counter to be recorded on the chip. Also, communication between dispenser and cartridge can be provided by a variety of technologies, such as infrared via IrDA, and magnetic switching. Data can also be transmitted using integrated GPRS or GPS modules to communicate with external networks.

Figure 2:
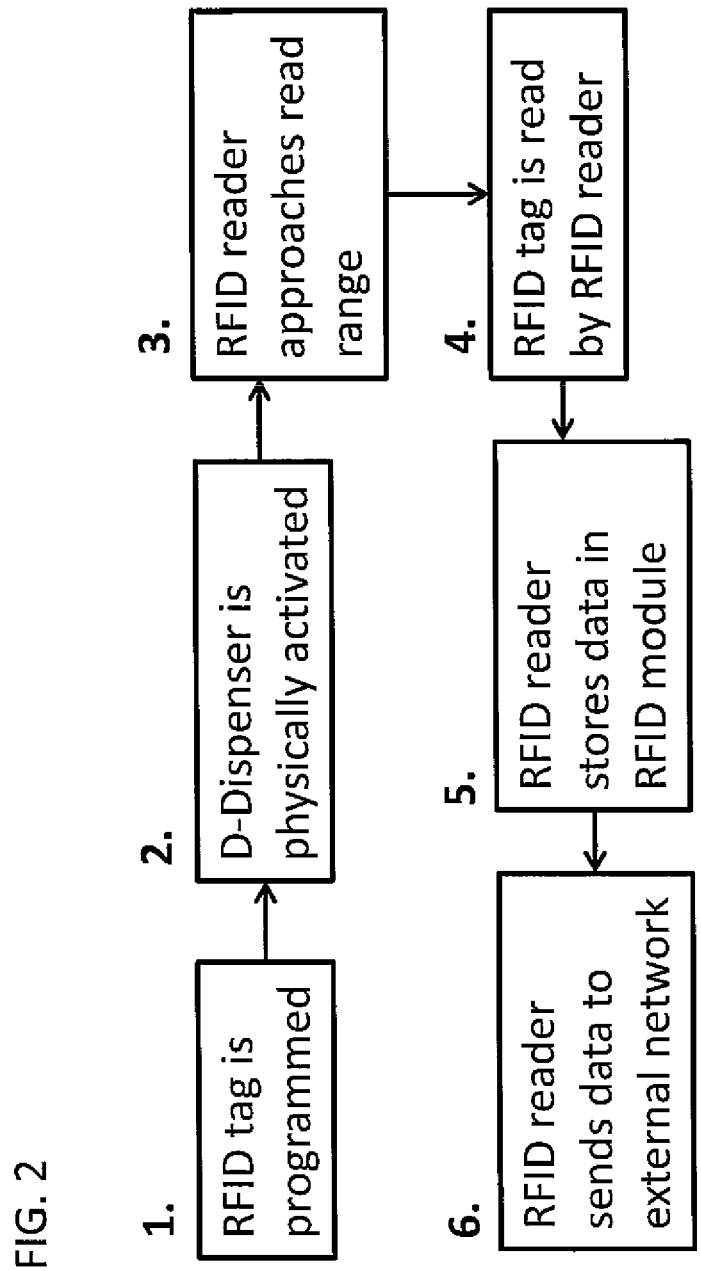
FIG. 2 illustrates a block diagrams indicating the steps involved in the process of medication dispensing and corresponding data processing in the D-Dispenser system.

FIG. 2 illustrates block diagrams indicating the steps involved in the process of medication dispensing and corresponding data processing in the D-Dispenser system. An RFID tag 50 of FIG. 1 is programmed step 1, to address content on the RFID chip. In operation of the D-Dispenser, the system is activated during normal use step 2. When the RFID reader 55 of FIG. 1 approaches the read range of the RFID tag step 3, the RFID tag is read by the RFID reader step 4. Following an RFID read, the RFID reader stores data in the RFID reader module step 5, and then RFID reader sends data beacon to an external network step 6.

An example of flow pathway of FIG. 2 of the D-Dispenser can be explained as follows:

As an aftermarket product, manufacturers of pharmaceuticals, nutritional, and any oral dosage formulated product can pre-program the RFID tag to contain product specific data step 1. The manufacturer sells pre-filled tablets with the RFID tag assembled onto cartridge. Additionally, the tag may be written with patient specific code at point of care site step 1. During patient use, button is pressed to activate the D-Dispenser step 2, due to proximity between the RFID reader module and the RFID tag. The RFID tag may also include data about how medication must be administered and read step 4. When the RFID reader module reads the cartridge RFID tag step 4, it internally verifies the prescription was intended for the patient's D-Dispenser. Recorded time stamps are stored on RFID reader module step 5, and transmitted to a hospital network step 6. If the medication regimen is not followed, the patient will be contacted with improved guidance. Alerts can also be used to simultaneously transmit data to pharmacies to automatically refill prescriptions and also charge the patient's account, and informing them when to pick up their new prescription.

Figure 3:
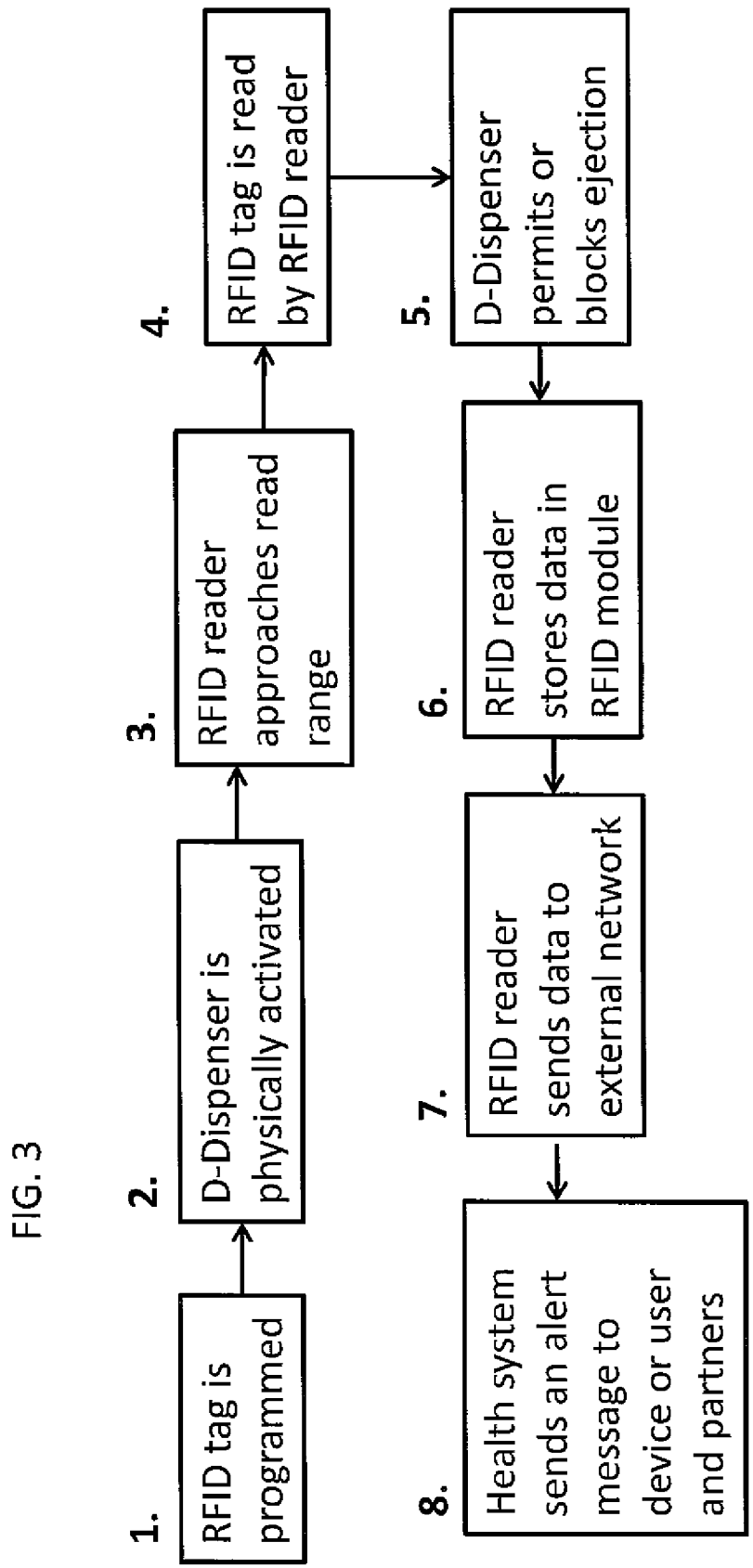
FIG. 3 illustrates a block diagram showing how the D-dispensers can operate with greater restrictive control.

FIG. 3 illustrates a block diagram showing how the D-Dispenser can operate with greater restrictive control. An RFID tag 50 of FIG. 1 is read programmed step 1, externally activated step 2, RFID approaches read range of RFID tag step 3, the RFID tag is ready by RFID reader St of FIG. 1 step 4, the D-Dispenser can decide to permit or block ejection of pills step 5, RFID reader stores data from the event step 6, RFID reader sends data of the process step 7, health system sends an alert message to device or user about updated program status step 8.

An example of flow pathway of FIG. 3 of the D-Dispenser can be explained as follows:

In the physician setting or hospital, a health practitioner can take field programmable RFID chips already attached to cartridges, and use software to compile RFID data on the tag, based on patient specific regimens step 1. Similarly, patients can receive their cartridge blank with addressed RFID chip, or pickup in the pharmacy for filling step 1. A nurse or caregivers activates the D-Dispenser by pressing the button after cross checking with the wristband patient tag step 2. The RFID reader comes into read range of the RFID tag step 3. After the RFID tag is read by RFID reader step 4, the medication prescribed to a given patient can be restricted only on the D-Dispenser step 5, to prevent medication abuse or errors. For example, a motor feature can be added to lock the button when the previous timestamp is shorter than required time delays for given medication, or when the RFID tag serial on the assigned medication cartridge mismatches the D-Dispenser, or when the RFID tag on the patient wrist band mismatches with the RFID tag on the Cartridge, coordinated via the D-Dispenser, enabling a lockout feature to prevent medication error, and abuse. The RFID history data is stored step 6, and sent to the network step 7. The master health system controlling patient monitoring can alert the appropriate partners, or D-Dispenser devices that there is a medical error requiring immediate correction step 8. For example, a critical alert can be sent to a mobile device, lock-out signal to the D-Dispenser, or an automatically triggered call can alert the patient to take critical medication as directed.

Although there has been hereinabove described a specific digital dispenser system in accordance with the present invention for the purpose of illustrating the manner in which the invention may be used to advantage, it should be appreciated that the invention is not limited thereto. That is, the present invention may suitably comprise, consist of or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A digital dispenser system, comprising:
    a rotatable cartridge for storing a supply of medication;
    a housing supporting the cartridge;
    the housing comprising a mechanical dispenser encompassing the cartridge and the cartridge encompassing and capturing the supply of medication separately from the housing and the mechanical dispenser, and the dispenser having a user activated button configured for manually dispensing medication out of said cartridge;
    wherein a translational movement of the user activated button during dispensing medication is aligned with a plane in which the cartridge rotates for dispensing medication, wherein a single translational movement of the user activated button both rotates the cartridge and also dispenses the medication through a cartridge peripheral opening and out of the housing for facilitating one-hand operation; and
    an electro-magnetic communication system established between said cartridge and the dispenser configured for relaying information about the medication stored or dispensed, wherein the communication system comprises a tag and a reader, where the tag is attached to either the cartridge or the button and the reader is attached to the other of either the cartridge or the button.

2. The system according to claim 1, wherein a physical relationship between the dispenser and the cartridge changes in coordination with the medication dispensing to allow dispensing registration.

3. The system according to claim 1, wherein the cartridge is rotatable in the mechanical dispenser and wherein the tag is disposed within a center of the rotatable cartridge.

4. The system according to claim 1, further comprising a lock out mechanism for preventing release of medication from the cartridge to prevent medication error.

5. The system according to claim 4, wherein the lock out mechanism is configured to control the button release for enabling or disenabling the button activation by a user.

6. The system according to claim 5, wherein the lock out mechanism includes a programmable control of the button release for enabling or disenabling the button activation by the user according to a medication regiment.

7. The system according to claim 1, further comprising a shutter for preventing release of medication from the cartridge to prevent medication error.

8. The system according to claim 1, further comprising a thermoelectric cooling system coupled to the cartridge to maintain the stored medication at a storage required temperature.

9. The system according to claim 1, wherein the dispenser button and opening for medication dispensing are disposed on opposite sides of said dispenser for facilitating one-hand operation of the dispenser system.

10. The system accordingly to claim 1, further comprising a second tag placed on the dispenser for the dispenser identification from an external reader.

11. A medication dispenser system comprising:
    a cartridge for storing a supply of medication;
    a housing supporting the cartridge;
    the housing comprising a mechanical dispenser encompassing the cartridge and the cartridge encompassing and capturing the supply of medication separately from the housing and the mechanical dispenser, and the dispenser having a user activated translational button for manually dispensing medication out of said cartridge through a cartridge peripheral opening;
    wherein a translational movement of the button during dispensing medication is align with a plane in which the cartridge rotates for dispensing medication, wherein a single translational movement of the button both rotates the cartridge and also dispenses the medication out of the cartridge and the housing for facilitating one-hand operation; and
    a wireless network communication system established between the dispenser and an external network configured for programming or collecting history data from the dispenser;
    a second communication system between the cartridge and the mechanical dispenser configured for relaying information about the medication stored or dispensed, wherein the second communication system comprises a RF tag associated with the cartridge and an RF reader associated with the mechanical dispenser.

12. The system according to claim 11, wherein the RF reader is attached to the user activatable button of the mechanical dispenser.

13. The system according to claim 11, further comprising a lock out mechanism for preventing release of medication from the cartridge to prevent medication error.

14. The system according to claim 11, further comprising a shutter for preventing release of medication from the cartridge to prevent medication error.

15. A digital dispenser system comprising:
    a movable cartridge for storing a supply of medication;
    a housing supporting the cartridge;
    the housing comprising a mechanical dispenser encompassing the cartridge and the cartridge encompassing the supply of medication and the dispenser having a user activated button configured for manually dispensing medication out of said cartridge, where the user activated button moves in a translational direction which is aligned with a plane of the movement of the cartridge, wherein a single user-activated button translational movement moves the cartridge and also dispenses the medication out of the cartridge through a cartridge peripheral opening and the housing for facilitating one-hand operation;

an electro-magnetic communication system established between the cartridge and the dispenser configured for relaying information about the medication stored or dispensed manually by a user, the communication system comprising a tag and a reader wherein the tag is attached to either the cartridge or the button and the reader is attached to the other of either the cartridge or the button; and a wireless network communication system established between the dispenser and an external network configured for programming or collecting history data from the dispenser.

16. A medication dispenser system comprising:

a cartridge for storing a supply of medication;

a housing supporting the cartridge;

the housing comprising a mechanical dispenser encompassing the cartridge and the cartridge encompassing the supply of medication and the dispenser having a user activated button for dispensing medication out of said cartridge;

wherein a single movement of the button both moves the cartridge and also dispenses the medication out of the cartridge and the housing; and an electro-magnetic communication system established between the cartridge and the button configured for relaying information about the medication stored or dispensed, wherein the communication system comprises a tag and a reader, where the tag is attached to either the cartridge or the button and the reader is attached to the other of either the cartridge or the button, wherein a physical relationship between the tag and the reader changes in coordination with the medication dispensing to allow dispensing registration by the electro-magnetic communication system.

17. A medication dispenser system comprising:

a cartridge for storing a supply of medication;

a housing supporting the cartridge;

the housing comprising a mechanical dispenser encompassing the cartridge and the cartridge encompassing and capturing the supply of medication separately from the housing and the mechanical dispenser, and the dispenser having a user activated button for dispensing medication out of said cartridge through a cartridge peripheral opening;

wherein a single movement of the button both rotates the cartridge and also dispenses the medication out of the cartridge and the housing for facilitating one-hand operation;

a wireless network communication system established between the dispenser and an external network configured for programming or collecting history data from the dispenser;

a lock out mechanism configured to lock the button preventing release of medication from the cartridge to prevent medication error; and an electro-magnetic communication system established between said cartridge and the dispenser configured for relaying information about the medication stored or dispensed, wherein the communication system comprises a tag and a reader, where the tag is attached to either the cartridge or the mechanical dispenser and the reader is attached to the other of either the cartridge or the mechanical dispenser.

\* \* \* \* \*